United States Patent [19]

Beller et al.

[11] Patent Number: 5,559,277
[45] Date of Patent: Sep. 24, 1996

[54] PROCESS FOR PREPARING BIPHENYLS USING PALLADACYCLES AS CATALYSTS

[75] Inventors: Matthias Beller, Niedernhausen; Wolfgang A. Herrmann, Freising; Christoph Brossmer, Frankfurt, all of Germany

[73] Assignee: Hoechst AG, Germany

[21] Appl. No.: 496,392

[22] Filed: Jun. 29, 1995

[30] Foreign Application Priority Data

Jul. 1, 1994 [DE] Germany .............. 44 23 061.3

[51] Int. Cl.$^6$ .................. C07C 255/50; C07C 253/30; C07C 1/32
[52] U.S. Cl. .............. 585/469; 585/457; 570/190
[58] Field of Search .................. 585/467, 469, 585/457, 425; 570/190

[56] References Cited

U.S. PATENT DOCUMENTS

| | | | |
|---|---|---|---|
| 4,294,976 | 10/1981 | Itatanu et al. | 548/425 |
| 5,130,439 | 7/1992 | Lo et al. | 548/110 |
| 5,159,082 | 10/1992 | Sato et al. | 585/425 |
| 5,254,776 | 10/1993 | Lang et al. | 570/190 |
| 5,451,703 | 9/1995 | Schach et al. | 545/469 |

FOREIGN PATENT DOCUMENTS

| | | |
|---|---|---|
| 0470795 | 2/1992 | European Pat. Off. |
| 91/09008 | 6/1991 | WIPO |
| 94/00423 | 1/1994 | WIPO |

Primary Examiner—Glenn A. Caldarola
Attorney, Agent, or Firm—Connolly & Hutz

[57] ABSTRACT

The invention relates to a process for preparing biphenyls of the formula (I)

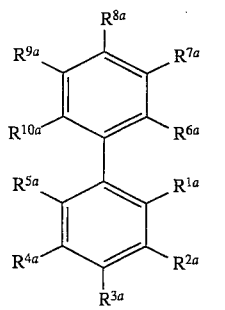

where $R^{1a}$ to $R^{10a}$ are, independently of one another, hydrogen, $C_1$–$C_{12}$-alkyl, $C_1$–$C_{12}$-alkenyl, $C_1$–$C_{12}$-alkynyl, alkoxy-($C_1$–$C_{12}$), acyloxy-($C_1$–$C_{12}$), O-phenyl, aryl, heteroaryl, fluorine, chlorine, OH, $NO_2$, CN, COOH, CHO, $SO_3H$, $SO_2R$, SOR, $NH_2$, NH-alkyl-($C_1$–$C_{12}$), N-alkyl$_2$-($C_1$–$C_{12}$), C-Hal$_3$, NHCO-alkyl-($C_1$–$C_8$), CONH-alkyl-($C_1$–$C_4$), CON-(alkyl)$_2$-($C_1$–$C_4$), COO-alkyl-($C_1$–$C_{12}$), $CONH_2$, CO-alkyl-($C_1$–$C_{12}$), NHCOH, NHCOO-alkyl-($C_1$–$C_8$), CO-phenyl, COO-phenyl, CHCHCO$_2$-alkyl-($C_1$–$C_{12}$), CHCHCO$_2$H, PO-phenyl$_2$, PO-alkyl$_2$-($C_1$–$C_8$), by reaction of haloaromatics or aryl sulfonates of the formula (II)

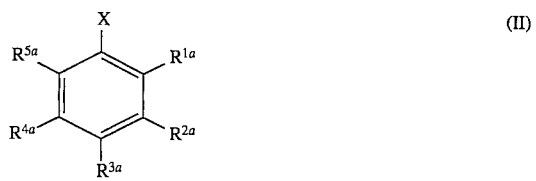

with arylboron derivatives of the formula III

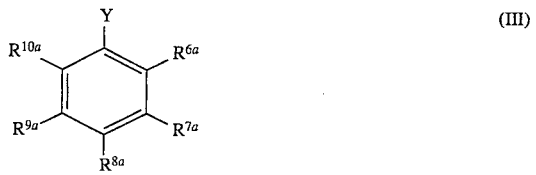

where $R^{1a}$ to $R^{10a}$ are as defined above and X is bromine, chlorine or $OSO_2CF_3$, $OSO_2$-aryl, $OSO_2$-alkyl and Y is $B(OH)_2$, B(O-alkyl)$_2$, B(O-aryl)$_2$, wherein a palladium compound of the formula (IV)

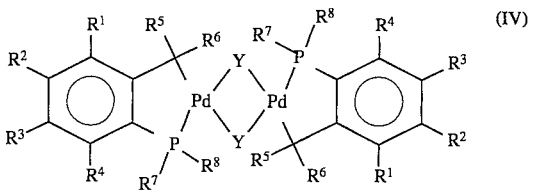

where $R^1$, $R^2$, $R^3$, $R^4$, $R^5$, $R^6$ are, independently of one another, hydrogen, ($C_1$–$C_4$)-alkyl, ($C_5$–$C_8$)-cycloalkyl, ($C_1$–$C_4$)-alkoxy, fluorine, $NH_2$, NH-alkyl($C_1$–$C_4$), N(alkyl)$_2$-($C_1$–$C_4$), CO$_2$-alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$, $R^8$ are ($C_1$–$C_8$)-alkyl, ($C_3$–$C_{12}$)-cycloalkyl, substituted or unsubstituted aryl and Y is an anion of an inorganic or organic acid, is used as catalyst.

18 Claims, No Drawings

PROCESS FOR PREPARING BIPHENYLS USING PALLADACYCLES AS CATALYSTS

The present invention relates to a new process for preparing biphenyls from aryl halides or aryl sulfonates and arylboronic acids using novel catalysts, so-called palladacycles.

Biphenyls are industrially important as fine chemicals for liquid crystals and related applications and as starting materials for active compound precursors, particularly as angiotensin antagonists.

A frequently used method of synthesizing biphenyls on a laboratory scale is the palladium-catalyzed cross-coupling (Suzuki coupling), in which iodoaromatics, bromoaromatics or aryl sulfonates are reacted with organometallic aryl derivatives, in particular arylboron derivatives, in the presence of palladium catalysts. Examples which describe this methodology are given in, for example, N. Miyaure, Y. Tanagi, A. Suzuki, Synthetic Communications, 11 (1981) 513, R. F. Heck, Palladium Reagents in Synthesis, Academic Press, London 1985, U.S. Pat. No. 5,130,439 and EP 470 795.

Despite the numerous publications in the field of the synthesis of biphenyls in the presence of palladium catalysts, no examples of a relatively large-scale industrial implementation of the methodology have hitherto been known. This can be attributed to the fact that the catalyst systems described frequently give satisfactory turnover numbers only with uneconomical starting materials such as iodoaromatics. Otherwise, in the case of bromoaromatics and, in particular, in the case of chloroaromatics, large amounts of catalyst generally have to be added, in general >1 mol %, to achieve industrially useful conversions. In addition, owing to the complexity of the reaction mixtures, simple catalyst recycling is not possible, so that catalyst costs generally make industrial implementation difficult. Furthermore, in the Suzuki coupling of substituted biphenyls using conventional catalyst systems such as Pd(OAc)$_2$/triphenylphosphine mixtures, aryl transfers from the corresponding phosphine are observed as a side reaction (D. F. O'Keefe et al., Tetrahedron Lett., 1992, 6679).

For the above reasons, it is of great industrial interest to find improved, industrially useful catalyst systems for the synthesis of biphenyls generally and, in particular, for the arylation of economically favorable bromoaromatics and chloroaromatics and aryl sulfonates. There was thus a great need for a process which avoids the disadvantages described and makes it possible to obtain biphenyls in high purity in a technically simple manner.

This object is achieved by a process for preparing biphenyls of the formula (I)

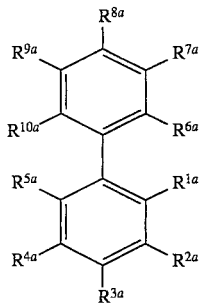

where $R^{1a}$ to $R^{10a}$ are, independently of one another, hydrogen, $C_1$–$C_{12}$-alkyl, $C_1$–$C_{12}$-alkenyl, $C_1$–$C_{12}$-alkynyl, alkoxy-($C_1$–$C_{12}$), acyloxy-($C_1$–$C_{12}$), O-phenyl, aryl, heteroaryl, fluorine, chlorine, OH, $NO_2$, CN, COOH, CHO, $SO_3H$, $SO_2R$, SOR, $NH_2$, NH-alkyl-($C_1$–$C_{12}$), N-alkyl$_2$-($C_1$–$C_{12}$), C-Hal$_3$, NHCO-alkyl-($C_1$–$C_8$), CONH-alkyl-($C_1$–$C_4$), CON-(alkyl)$_2$-($C_1$–$C_4$), COO-alkyl-($C_1$–$C_{12}$), $CONH_2$, CO-alkyl-($C_1$–$C_{12}$), NHCOH, NHCOO-alkyl-($C_1$–$C_8$), CO-phenyl, COO-phenyl, CHCHCO$_2$-alkyl-($C_1$–$C_{12}$), CHCHCO$_2$H, PO-phenyl$_2$, PO-alkyl$_2$-($C_1$–$C_8$), by reaction of haloaromatics or aryl sulfonates of the formula (II)

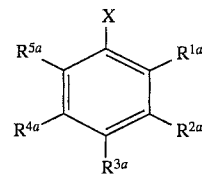

with arylboron derivatives of the formula III

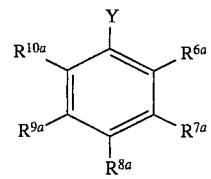

where $R^{1a}$ to $R^{10a}$ are as defined above and X is bromine, chlorine or $OSO_2CF_3$, $OSO_2$-aryl, $OSO_2$-alkyl and Y is $B(OH)_2$, $B(O$-alkyl$)_2$, $B(O$-aryl$)_2$, wherein a palladium compound of the formula (IV)

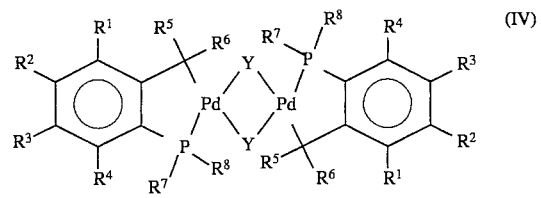

where $R^1$, $R^2$, $R^3$, $R^4$, $R^5$, $R^6$ are, independently of one another, hydrogen, ($C_1$–$C_4$)-alkyl, ($C_5$–$C_8$)-cycloalkyl, ($C_1$–$C_4$)-alkoxy, fluorine, $NH_2$, NH-alkyl($C_1$–$C_4$), N(alkyl)$_2$, ($C_1$–$C_4$), CO$_2$-alkyl-($C_1$–$C_4$), OCO-alkyl-($C_1$–$C_4$) or phenyl, or $R^1$ and $R^2$, $R^2$ and $R^3$, $R^3$ and $R^4$, $R^5$ and $R^6$ together form an aliphatic or aromatic ring, and $R^7$, $R^8$ are ($C_1$–$C_8$)-alkyl, ($C_3$–$C_{12}$)-cycloalkyl, substituted or unsubstituted aryl and Y is an anion of an inorganic or organic acid, is used as catalyst.

The process is of interest for preparing compounds of the formula (I) in which $R^{1a}$ to $R^{10a}$ are hydrogen, $C_1$–$C_8$-alkyl, CN, CO$_2$H, CHO, COO-alkyl-($C_1$–$C_8$), phenyl, 5-ring heteroaryl, 6-ring heteroaryl, $CONH_2$, CONH-alkyl-($C_1$–$C_4$), CON-(alkyl)$_2$, ($C_1$–$C_4$), $NO_2$, CO-alkyl-($C_1$–$C_4$), F, Cl, OH, O-alkyl-($C_1$–$C_4$), $NH_2$, NHCO-alkyl-($C_1$–$C_4$).

Important compounds are also those of the formula (I) in which 4, in particular 6, preferably 8, of the substituents $R^{1a}$ to $R^{10a}$ are hydrogen and the remaining substituents are as defined above.

The process is of great importance, for example, for preparing the compounds 4-alkyl-2'-cyanobiphenyl, 4-alkyl-2'-biphenylcarboxylic acid, 4-alkyl- 2'-biphenylcarboxylic ester, 4-alkyl-2'-biphenylcarboxamide, 4-alkyl-2'-biphenylaldehyde, 4-alkyl-2 '-heteroarylbiphenyl.

In many cases, compounds of the formula (IV) in which $R^1$ to $R^6$ are hydrogen, alkyl ($C_1$–$C_4$), phenyl, cycloalkyl-($C_5$–$C_8$), $R^7$ and $R^8$ are phenyl, tolyl, xylyl, mesityl, alkyl($C_1$–$C_8$) and cycloalkyl($C_5$–$C_8$) and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate or pyrazolyl have been found to be useful.

Well suited compounds are, for example, also those of the formula IV in which $R^1$–$R^6$ are H, $(C_1$–$C_4)$-alkyl, phenyl and $R^7$, $R^8$ are $(C_1$–$C_8)$-alkyl, phenyl, tolyl, mesityl and xylyl.

Very good results are given by the compounds:

trans-di-μ-acetato-bis[o-(di-o-tolylphosphino)benzyl]dipalladium(II)

trans-di-μ-chloro-bis[o-(di-o-tolylphosphino)benzyl]dipalladium(II)

trans-di-μ-bromo-bis[o-(di-o-tolylphosphino)benzyl]dipalladium(II)

trans-di-μ-iodo-bis[o-(di-o-tolylphosphino)benzyl]dipalladium(II)

trans-di-μ-acetato-bis[o-(dimesitylphosphino)- 3,5-dimethylbenzyl]dipalladium(II)

trans-di-μ-chloro-bis[o-(dimesitylphosphino)- 3,5-dimethylbenzyl]dipalladium(II)

trans-di-μ-bromo-bis[o-(dimesitylphosphino)- 3,5-dimethylbenzyl]dipalladium(II)

trans-di-μ-iodo-bis[o-(dimesitylphosphino)- 3,5-dimethylbenzyl]dipalladium(II)

trans-di-μ-acetato-bis[o-(t-butyl-o-tolylphosphino)benzyl]dipalladium(II)

trans-di-μ-acetato-bis[o-(di-t-butylphosphino)benzyl]dipalladium(II)

trans-di-μ-acetato-bis[o-(cyclohexyl-o-tolylphosphino)benzyl]dipalladium(II)

Solvents used are generally inert organic solvents. Preference is given to using aromatic, dipolar aprotic and polar solvents such as alkylbenzenes, dialkylbenzenes and trialkylbenzenes, ethers, esters of aliphatic carboxylic acids, dialkyl sulfoxides, N,N-dialkylamides of aliphatic carboxylic acids or alkylated lactams, amines and alcohols.

Since hydrogen halide is eliminated in the reaction, it is advantageous to neutralize this hydrogen halide by adding a base. Suitable bases for this purpose are primary, secondary or tertiary amines such as alkylamines, dialkylamines, trialkylamines, which can be alicyclic or open-chain, and alkali metal or alkaline earth metal salts of aliphatic or aromatic carboxylic acids or of carbonic acid, such as sodium, potassium, calcium, magnesium acetate and corresponding carbonates or hydrogencarbonates and also alkali metal or alkaline earth metal hydroxides.

The palladium catalysts used are generally synthesized separately prior to the actual reaction, but they can also, in certain cases, be generated in situ without loss of catalytic activity.

The process is generally carried out at temperatures of from 20° to 200° C. Temperatures of from 60° to 180° C., in particular from 100° to 150° C., have been found to be useful.

The synthesis of the palladium catalysts used is carried out by a method similar to that of German Patent Application No. P 4421 753.6.

The palladacycles which are used or which form generally have dimeric character. However, in the case of certain compounds, monomeric or polymeric structures can also be present.

Catalysts used for the purposes of the reaction of aryl halides with organometallic aryl derivatives are generally palladium compounds. Although both palladium(II) and palladium(0) complexes are used in Heck reactions, it is generally accepted that only palladium(0) compounds are the actual catalysts of the reaction. Compounds formulated here are frequently coordinatively unsaturated 14-electron palladium(0) species which are in general stabilized with weak donor ligands such as phosphines.

The following examples serve to illustrate the process of the invention, without restricting it to them.

Example 1

165 mmol of bromobenzonitrile, 247 mmol of phenylboronic acid, 330 mmol of potassium carbonate are heated with 0.2 mol % of trans-di-acetato-bis[o-(di-o-tolylphosphino)benzyl]dipalladium(II) in 300 ml of xylene for 16 hours at 130° C. The reaction solution is distilled after aqueous workup.

Yield: 93% of 2-cyanobiphenyl.

Example 2

165 mmol of bromobenzonitrile, 247 mmol of 4-methylphenylboronic acid, 330 mmol of potassium carbonate are heated with 0.2 mol % of trans-di-acetato-bis[o-(di-o-tolylphosphino)benzyl]dipalladium(II) in 300 ml of xylene for 16 hours at 130° C. The reaction solution is distilled after aqueous workup.

Yield: 94% of 2-cyano-4-methylbiphenyl.

Example 3

157 mmol of bromoacetophenone, 236 mmol of phenylboronic acid, 314 mmol of potassium carbonate are heated with 0.2 mol % of trans-di-acetato-bis[o-(di-o-tolylphosphino)benzyl]dipalladium(II) in 300 ml of xylene for 16 hours at 130° C. The reaction solution is recrystallized after aqueous workup.

Yield: 94% of 4-acetylbiphenyl.

Example 4

55.6 g of chloroacetophenone, 1.5 mol equivalents of phenylboronic acid, 2.0 mol equivalents of potassium carbonate are heated with 0.1 mol % of trans-di-acetato-bis[o-(di-o-tolylphosphino)benzyl]dipalladium(II) in 300 ml of xylene for 16 hours at 130° C. The reaction solution is recrystallized after aqueous workup.

Yield: 81% of 4-acetylbiphenyl.

Example 5

20 mmol of 2,4-dichloro-5-fluorobromobenzene, 180 mmol of phenylboronic acid, 240 mmol of potassium carbonate are heated with 0.1 mol % of trans-di-acetato-bis[o-(di-o-tolylphosphino)benzyl]dipalladium(II) in 300 ml of xylene for 16 hours at 130° C. The reaction solution is recrystallized after aqueous workup.

Yield: 84% of 2,4-dichloro-5-fluorobiphenyl.

Example 6

157 mmol of 4-fluorobromobenzene, 236 mmol of phenylboronic acid, 314 mmol of potassium carbonate are heated with 0.1 mol % of trans-di-acetato-bis[o-(di-o-tolylphosphino)benzyl]dipalladium(II) in 300 ml of xylene for 16 hours at 130° C. The reaction solution is distilled after aqueous workup.

Yield: 91% of 4-fluorobiphenyl.

Example 7

157 mmol of 2-chlorobenzonitrile, 236 mmol of 4-methylphenylboronic acid, 314 mmol of potassium carbonate are heated with 0.2 mol % of trans-di-acetato-bis[o-(di-o- tolylphosphino)benzyl]dipalladium(II) in 300 ml of xylene for 16 hours at 130° C. The reaction solution is recrystallized after aqueous workup.

Yield: 73% of 2-cyano-4-methylbiphenyl.

Example 8 Catalyst prepared in situ 55.6 g of chloroacetophenone, 1.5 mol equivalents of phenylboronic acid, 2.0 mol equivalents of potassium carbonate are heated with 0.1 mol % of palladium acetate and 0.1 mol % of tri-o-tolylphosphine in 300 ml of xylene for 16 hours at 130° C. The reaction solution is recrystallized after aqueous workup.

Yield: 65% of 4-acetylbiphenyl.

General procedure for Examples 9 to 15

100 mmol of the corresponding aryl halide, 150 mmol of phenylboronic acid and 200 mmol of potassium carbonate are heated with 0.1 mmol of palladacycle in 200 ml of xylene for 16 hours at 130° C. The cooled reaction mixture is subsequently extracted twice with 100 ml of water and the organic phase is separated off. The solvent is taken off in vacuo and the crude product is further purified by distillation or recrystallization.

Example 9

Aryl halide: 2-bromobenzonitrile, catalyst: trans-di-μ-acetato-bis[o-(di-o-tolylphosphino)benzyl]dipalladium(II)
Yield: 92% of 2-cyanobiphenyl.

Example 10

Aryl halide: 4-bromobenzaldehyde; catalyst: trans-di-μ-acetato-bis[o-(di-t-butylphosphino)benzyl]dipalladium(II)
Yield: 95% of 4-formylbiphenyl.

Example 11

Aryl halide: 4-bromobenzaldehyde; catalyst: trans-di-μ-acetato-bis[o-(cyclohexyl-o-tolylphosphino)benzyl]dipalladium(II)
Yield: 93% of 4-formylbiphenyl.

Example 12

Aryl halide: 4-bromobenzaldehyde; catalyst: trans-di-μ-bromo-bis[o-(dimesitylphosphino)-3,5-dimethylbenzyl]dipalladium(II)
Yield: 98% of 4-formylbiphenyl.

Example 13

Aryl halide: 4-bromobenzaldehyde; catalyst: trans-di-μ-bromo-bis[o-(di-o-tolylphosphino)benzyl]dipalladium(II)
Yield: 90% of 4-formylbiphenyl.

Example 14

Aryl halide: 4-bromobenzaldehyde; catalyst: trans-di-μ-acetato-bis[o-(cyclohexyl-o-tolylphosphino)benzyl]dipalladium(II)
Yield: 78% of 4-formylbiphenyl.

Example 15

Aryl halide: 2-fluorobenzene; catalyst: trans-di-μ-bromo-bis[o-(di-o-tolylphosphino)benzyl]dipalladium(II)
Yield: 82% of 2-fluorobiphenyl.

Example 16

15.1 mmol of 4-bromoanisole, 22.5 mmol of phenylboronic acid, 33 mmol of potassium carbonate are heated with 0.001 mmol of bis(di-o-tolylphosphinobenzyl)palladium acetate in 60 ml of xylene at 140° C. until reaction is complete. After aqueous workup and crystallization, the product is obtained.

Yield: 73% of 4-methoxybiphenyl.

We claim:

1. A process for preparing biphenyls of the formula (I)

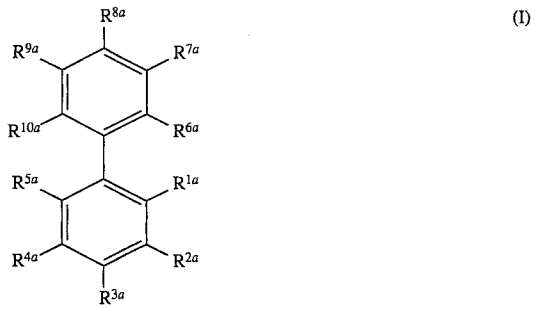

where $R^{1a}$ to $R^{10a}$ are, independently of one another, hydrogen, $C_1$–$C_{12}$-alkyl, $C_1$–$C_{12}$-alkenyl, $C_1$–$C_{12}$-alkynyl, alkoxy-($C_1$–$C_{12}$), acyloxy-($C_1$–$C_{12}$), O-phenyl, phenyl, tolyl, xylyl, mesityl, fluorine, chlorine, OH, $NO_2$, CN, COOH, CHO, $SO_3H$, $NH_2$, NH-alkyl-($C_1$–$C_{12}$), N-alkyl$_2$-($C_1$–$C_{12}$), C-Hal$_3$, NHCO-alkyl-($C_1$–$C_8$), CONH-alkyl-($C_1$–$C_4$), CON-(alkyl)$_2$-($C_1$–$C_4$), COO-alkyl-($C_1$–$C_{12}$), $CONH_2$, CO-alkyl-($C_1$–$C_{12}$), NHCOH, NHCOO-alkyl-($C_1$–$C_8$), CO-phenyl, COO-phenyl, CHCHCO$_2$-alkyl-($C_1$–$C_{12}$), CHCHCO$_2$H, PO-phenyl$_2$, PO-alkyl$_2$-($C_1$–$C_8$), which comprises a reaction of haloaromatics or aryl sulfonates of the formula (II)

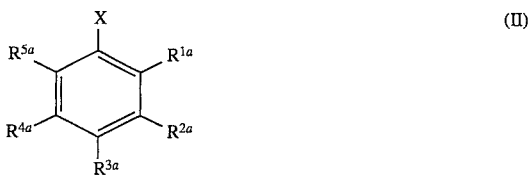

with arylboron derivatives of the formula III

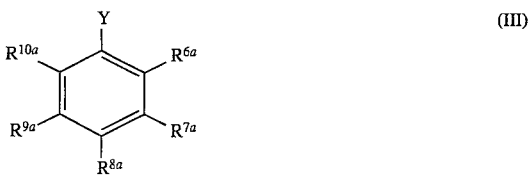

where $R^{1a}$ to $R^{10a}$ are as defined above and X is bromine, chlorine, $OSO_2CF_3$, $OSO_2$-aryl or $OSO_2$-alkyl and Y is $B(OH)_2$, $B(O\text{-alkyl})_2$, $B(O\text{-aryl})_2$, and a catalyst comprising a palladium compound of the formula (IV)

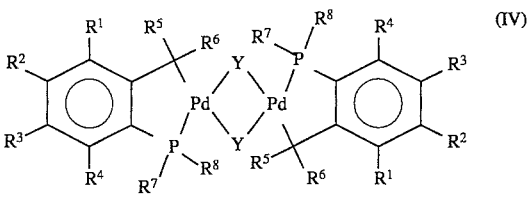

where $R^1$, $R^2$, $R^3$, $R^4$, $R^5$ and $R^6$ are, independently of one another, hydrogen, ($C_1$–$C_4$)-alkyl, ($C_5$–$C_8$)-cycloalkyl, ($C_1$–$C_4$)-alkoxy, fluorine, $NH_2$, NH-alkyl($C_1$–$C_4$), N(alkyl)$_2$-($C_1$–$C_4$), CO$_2$-alkyl-($C_1$–$C_4$), OCO-alkyl- ($C_1$–$C_4$) or phenyl, or $R^1$ and $R^2$, $R^2$ and $R^3$, $R^3$ and $R^4$ or $R^5$ and $R^6$ together form an aliphatic or aromatic ring, and $R^7$ and $R^8$ are, independently of one another, ($C_1$–$C_8$)-alkyl, ($C_3$–$C_{12}$)-cycloalkyl, substituted or unsubstituted aryl and Y is acetate, propionate, benzoate, chloride, bromide, iodide, fluoride, sulfate, hydrogensulfate, nitrate, phosphate, tetrafluoroborate, tosylate, mesylate, acetylacetonate, hexafluoroacetylacetonate or pyrazolyl.

2. The process as claimed in claim 1, wherein, in formula (IV), $R^1$ to $R^6$ are, independently of one another, hydrogen, ($C_1$–$C_4$)-alkyl, ($C_5$–$C_8$-cycloalkyl, $R^7$ and $R^8$, independently of one another, are phenyl, tolyl, xylyl, mesityl, alkyl-($C_1$–$C_8$, cycloalkyl-($C_5$–$C_8$) and Y is acetate, propionate, benzoate, chloride, bromine, iodide, fluoride, sulfate, hydrogensulfate, nitrate, phosphate, tetrafluoroborate, tosylate, mesylate, acetylacetonate, hexafluoroacetylacetonate or pyrazolyl.

3. The process as claimed in claim 1, wherein, in formula (IV), $R^1$ to $R^6$, independently of one another, are H, ($C_1$–$C_4$)-alkyl, phenyl, $R^7$ and $R^8$, independently of one another, are ($C_1$–$C_8$)-alkyl, phenyl tolyl, mesityl or xylyl.

4. The process as claimed in claim 1, wherein the catalyst used is one of the compounds trans-di-μ-acetato-bis[o-(di-o-tolylphosphino)benzyl]dipalladium(II)

trans-di-μ-chloro-bis[o-(di-o-tolylphosphino)benzyl]dipalladium(II)

trans-di-μ-bromo-bis[o-(di-o-tolylphosphino)benzyl]dipalladium(II)

trans-di-μ-iodo-bis[o-(di-o-tolylphosphino)benzyl]dipalladium(II)

trans-di-μ-acetato-bis[o-(dimesitylphosphino)- 3,5-dimethylbenzyl]dipalladium(II)

trans-di-μ-chloro-bis[o-(dimesitylphosphino)- 3,5-dimethylbenzyl]dipalladium(II)

trans-di-μ-bromo-bis[o-(dimesitylphosphino)- 3,5-dimethylbenzyl]dipalladium(II)

trans-di-μ-iodo-bis[o-(dimesitylphosphino)- 3,5-dimethylbenzyl]dipalladium(II)

trans-di-μ-acetato-bis[o-(t-butyl-o-tolylphosphino)benzyl]dipalladium(II)

trans-di-μ-acetato-bis[o-(di-t-butylphosphino)benzyl]dipalladium(II)

trans-di-μ-acetato-bis[o-(cyclohexyl-o-tolylphosphino)benzyl]dipalladium(II).

5. The process as claimed in claim 1, wherein $R^{1a}$ to $R^{10a}$ in formula (I) are, independently of one another, hydrogen, ($C_1$–$C_8$)-alkyl, CN, $CO_2H$, CHO, COO-alkyl-($C_1$–$C_8$), phenyl, $CONH_2$, CONH-alkyl-($C_1$–$C_4$), CON-(alkyl)$_2$-($C_1$–$C_4$), $NO_2$, CO-alkyl-($C_1$–$C_4$), F, Cl, OH, O-alkyl-($C_1$–$C_4$), $NH_2$ or NHCO-alkyl-($C_1$–$C_4$).

6. The process as claimed in claim 1, wherein at least 4 of the substituents $R^{1a}$ to $R^{10a}$ are hydrogen.

7. The process as claimed in claim 1, wherein the compound of formula (I) is 4-alkyl-2'-cyanobiphenyl, 4-alkyl-2'-biphenylcarboxylic acid, 4-alkyl-2'-biphenylcarboxylic ester, 4-alkyl-2'-biphenylcarboxamide or 4-alkyl-2'-biphenyl-aldehyde.

8. The process as claimed in claim 1, which further comprises a solvent wherein said solvent is aromatic, dipolar aprotic or a polar solvent.

9. The process as claimed in claim 1, wherein an acid HX formed in the reaction is neutralized by adding a base and X is defined in claim 1.

10. The process as claimed in claim 9, wherein the base used is an alkylamine or a carbonate, hydrogencarbonate or acetate of lithium, sodium, potassium, calcium or magnesium.

11. The process as claimed in claim 1, wherein the reaction is carried out at temperatures of from 20° to 200° C.

12. The process as claimed in claim 1, wherein the catalyst is selected from the group consisting of trans-di-μ-acetato-bis{o-(di-o-tolylphosphino)benzyl}dipalladium(II), trans-di-μ-chloro-bis{o-(di-o-tolylphosphino)benzyl}dipalladium(II), trans-di-μ-bromo-bis{o-(di-o-tolylphosphino)benzyl}dipalladium(II), trans-di-μ-iodo-bis{o-(di-o-tolylphosphino)benzyl}dipalladium(II), trans-di-μ-acetato-bis{o-(dimesitylphosphino)- 3,5-dimethylbenzyl}dipalladium(II), trans-di-μ-chloro-bis{o-(dimesitylphosphino)- 3,5-dimethylbenzyl}dipalladium(II), trans-di-μ-bromo-bis{o-(dimesitylphosphino)- 3,5-dimethylbenzyl}dipalladium(II), trans-di-μ-iodo-bis{o-(dimesitylphosphino)- 3,5-dimethylbenzyl}dipalladium(II), trans-di-μ-acetato-bis{o-(t-butyl-o-tolylphosphino)benzyl}dipalladium(II), trans-di-μ-acetato-bis{o-(di-t-butylphosphino)benzyl}dipalladium(II) and trans-di-μ-acetato-bis{o-(cyclohexyl-o-tolylphosphino)benzyl}dipalladium(II).

13. The process as claimed in claim 6, wherein 6 of the substitutes $R^{1a}$ to $R^{10a}$ are hydrogen.

14. The process as claimed in claim 6, wherein 8 of the substitutes $R^{1a}$ to $R^{10a}$ are hydrogen.

15. The process as claimed in claim 8, wherein the solvents are selected from the group consisting of alkylbenzenes, dialkylbenzenes, trialkylbenzenes, ethers, esters of aliphatic carboxylic acids, dialkyl sulfoxides, N,N-dialkylamides of aliphatic carboxylic acids, alkylated lactams, amines and alcohols.

16. The process as claimed in claim 9, wherein the acid HX formed in the reaction is neutralized by adding an amine, an alkali metal salt of a weak acid or alkaline earth metal salt of a weak acid.

17. The process as claimed in claim 11, wherein the reaction temperature is carried out from 60° to 180° C.

18. The process as claimed in claim 12, wherein the reaction is carried out at a temperature from 100° to 150° C.

* * * * *